(12) United States Patent
Chavan et al.

(10) Patent No.: US 7,616,990 B2
(45) Date of Patent: Nov. 10, 2009

(54) IMPLANTABLE AND RECHARGEABLE NEURAL STIMULATOR

(75) Inventors: Abhi Chavan, Maple Grove, MN (US); Anthony Caparso, St. Louis Park, MN (US); Avram Scheiner, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 396 days.

(21) Appl. No.: 11/256,907

(22) Filed: Oct. 24, 2005

(65) Prior Publication Data

US 2007/0093875 A1    Apr. 26, 2007

(51) Int. Cl.
*A61N 1/00*    (2006.01)
(52) U.S. Cl. .......................................................... 607/2
(58) Field of Classification Search ...................... 607/2, 607/9, 27, 49; 600/459, 309; 429/162
See application file for complete search history.

(56) References Cited

U.S. PATENT DOCUMENTS

| | | | |
|---|---|---|---|
| 3,692,027 A | 9/1972 | Ellinwood Jr. | |
| 4,003,379 A | 1/1977 | Ellinwood, Jr. | |
| 4,082,097 A | 4/1978 | Mann et al. | |
| 4,146,029 A | 3/1979 | Ellinwood, Jr. | |
| 4,522,208 A * | 6/1985 | Buffet .......................... | 607/27 |
| 4,871,351 A | 10/1989 | Feingold | |
| 4,944,299 A | 7/1990 | Silvian | |
| 4,987,897 A | 1/1991 | Funke | |
| 5,042,497 A | 8/1991 | Shapland | |
| 5,052,388 A | 10/1991 | Sivula et al. | |
| 5,111,815 A | 5/1992 | Mower | |
| 5,199,428 A | 4/1993 | Obel et al. | |
| 5,203,326 A | 4/1993 | Collins | |
| 5,300,875 A | 4/1994 | Tuttle | |
| 5,318,592 A | 6/1994 | Schaldach | |
| 5,324,316 A | 6/1994 | Schulman et al. | |
| 5,330,507 A | 7/1994 | Schwartz | |
| 5,342,408 A | 8/1994 | deCoriolis et al. | |
| 5,354,318 A | 10/1994 | Taepke | |

(Continued)

FOREIGN PATENT DOCUMENTS

EP    0467695 A2    1/1992

(Continued)

OTHER PUBLICATIONS

"International Search Report and Written Opinion for Application No. PCT/US2006/041569", (Mar. 7, 2007),14.

(Continued)

*Primary Examiner*—George Manuel
(74) *Attorney, Agent, or Firm*—Schwegman, Lundberg, & Woessner, P.A.

(57) ABSTRACT

One aspect of the present subject matter relates to an implantable medical device. An embodiment of the device comprises a rechargeable power supply adapted to be recharged through an ultrasound signal, a neural stimulator connected to the rechargeable power supply, and a controller connected to the rechargeable power supply. The neural stimulator is adapted to generate a neural stimulation signal for delivery to a neural stimulation target through an electrode. The controller is further connected to the neural stimulator to control the neural stimulator according to a neural stimulation protocol. Other aspects are provided herein.

23 Claims, 4 Drawing Sheets

U.S. PATENT DOCUMENTS

| | | | |
|---|---|---|---|
| 5,436,548 A | 7/1995 | Thomas | |
| 5,496,360 A | 3/1996 | Hoffmann et al. | |
| 5,522,854 A | 6/1996 | Ideker et al. | |
| 5,540,730 A | 7/1996 | Terry, Jr. et al. | |
| 5,551,953 A | 9/1996 | Lattin et al. | |
| 5,562,711 A | 10/1996 | Yerich et al. | |
| 5,562,713 A | 10/1996 | Silvian | |
| 5,578,061 A | 11/1996 | Stroetmann et al. | |
| 5,662,689 A | 9/1997 | Elsberry et al. | |
| 5,700,282 A | 12/1997 | Zabara | |
| 5,707,400 A | 1/1998 | Terry, Jr. et al. | |
| 5,775,338 A | 7/1998 | Hastings | |
| 5,800,498 A | 9/1998 | Obino et al. | |
| 5,814,089 A | 9/1998 | Stokes et al. | |
| 5,843,142 A * | 12/1998 | Sultan | 607/49 |
| 5,846,218 A | 12/1998 | Brisken et al. | |
| 5,916,239 A | 6/1999 | Geddes et al. | |
| 5,972,029 A | 10/1999 | Fuisz | |
| 6,006,134 A | 12/1999 | Hill et al. | |
| 6,073,048 A | 6/2000 | Kieval et al. | |
| 6,115,636 A | 9/2000 | Ryan | |
| 6,117,085 A * | 9/2000 | Picatti et al. | 600/459 |
| 6,140,740 A | 10/2000 | Porat et al. | |
| 6,141,588 A * | 10/2000 | Cox et al. | 607/9 |
| 6,164,284 A | 12/2000 | Schulman et al. | |
| 6,206,914 B1 | 3/2001 | Soykan et al. | |
| 6,213,942 B1 | 4/2001 | Flach et al. | |
| 6,231,516 B1 | 5/2001 | Keilman et al. | |
| 6,237,398 B1 | 5/2001 | Porat et al. | |
| 6,240,316 B1 | 5/2001 | Richmond et al. | |
| 6,292,703 B1 | 9/2001 | Meier et al. | |
| 6,358,202 B1 | 3/2002 | Arent | |
| 6,445,953 B1 | 9/2002 | Bulkes et al. | |
| 6,453,195 B1 | 9/2002 | Thompson | |
| 6,456,866 B1 | 9/2002 | Tyler et al. | |
| 6,511,500 B1 | 1/2003 | Rahme | |
| 6,518,245 B1 | 2/2003 | Anderson et al. | |
| 6,519,488 B2 | 2/2003 | KenKnight et al. | |
| 6,522,926 B1 | 2/2003 | Kieval et al. | |
| 6,584,362 B1 | 6/2003 | Scheiner et al. | |
| 6,622,041 B2 | 9/2003 | Terry, Jr. et al. | |
| 6,645,145 B1 | 11/2003 | Dreschel et al. | |
| 6,788,970 B1 | 9/2004 | Park et al. | |
| 6,798,716 B1 | 9/2004 | Charych | |
| 6,802,811 B1 * | 10/2004 | Slepian | 600/309 |
| 6,804,561 B2 | 10/2004 | Stover | |
| 6,805,998 B2 * | 10/2004 | Jenson et al. | 429/162 |
| RE38,705 E | 2/2005 | Hill et al. | |
| 6,934,583 B2 | 8/2005 | Weinberg et al. | |
| 7,294,334 B1 | 11/2007 | Michal et al. | |
| 2002/0004670 A1 | 1/2002 | Florio et al. | |
| 2002/0026221 A1 | 2/2002 | Hill et al. | |
| 2002/0026222 A1 | 2/2002 | Schauerte et al. | |
| 2002/0042637 A1 | 4/2002 | Stover | |
| 2002/0072776 A1 | 6/2002 | Osorio et al. | |
| 2002/0107557 A1 | 8/2002 | Edell et al. | |
| 2002/0161410 A1 | 10/2002 | Kramer et al. | |
| 2002/0165586 A1 | 11/2002 | Hill et al. | |
| 2002/0183237 A1 | 12/2002 | Puskas | |
| 2002/0183793 A1 | 12/2002 | Struble et al. | |
| 2002/0198570 A1 | 12/2002 | Puskas | |
| 2003/0023279 A1 | 1/2003 | Spinelli et al. | |
| 2003/0045909 A1 | 3/2003 | Gross et al. | |
| 2003/0060848 A1 | 3/2003 | Kieval et al. | |
| 2003/0060858 A1 | 3/2003 | Kieval et al. | |
| 2003/0074039 A1 | 4/2003 | Puskas | |
| 2003/0078623 A1 | 4/2003 | Weinberg et al. | |
| 2003/0078629 A1 | 4/2003 | Chen | |
| 2003/0100924 A1 | 5/2003 | Foreman et al. | |
| 2003/0114905 A1 | 6/2003 | Kuzma | |
| 2003/0132731 A1 | 7/2003 | Chung | |
| 2003/0158584 A1 | 8/2003 | Cates | |
| 2003/0195578 A1 | 10/2003 | Perron et al. | |
| 2003/0212440 A1 | 11/2003 | Boveja | |
| 2004/0122477 A1 | 6/2004 | Whitehurst et al. | |
| 2004/0186531 A1 | 9/2004 | Jahns et al. | |
| 2004/0220621 A1 | 11/2004 | Zhou et al. | |
| 2005/0085864 A1 | 4/2005 | Schulman et al. | |
| 2005/0096705 A1 | 5/2005 | Pastore et al. | |
| 2005/0143779 A1 | 6/2005 | Libbus | |
| 2005/0143785 A1 | 6/2005 | Libbus | |
| 2005/0143787 A1 | 6/2005 | Boveja et al. | |
| 2005/0149126 A1 | 7/2005 | Libbus | |
| 2005/0149127 A1 | 7/2005 | Libbus | |
| 2005/0149128 A1 | 7/2005 | Heil, Jr. et al. | |
| 2005/0149129 A1 | 7/2005 | Libbus et al. | |
| 2005/0149130 A1 | 7/2005 | Libbus | |
| 2005/0149131 A1 | 7/2005 | Libbus et al. | |
| 2005/0149132 A1 | 7/2005 | Libbus | |
| 2005/0149133 A1 | 7/2005 | Libbus et al. | |
| 2005/0149143 A1 | 7/2005 | Libbus et al. | |
| 2005/0149155 A1 | 7/2005 | Scheiner et al. | |
| 2005/0149156 A1 | 7/2005 | Libbus et al. | |
| 2005/0187584 A1 | 8/2005 | Denker et al. | |
| 2006/0079945 A1 | 4/2006 | Libbus | |
| 2006/0229677 A1 | 10/2006 | Moffitt et al. | |

FOREIGN PATENT DOCUMENTS

| | | |
|---|---|---|
| EP | 0547734 A2 | 6/1993 |
| EP | 1304135 A2 | 4/2003 |
| EP | 1486232 A2 | 12/2004 |
| EP | 1541193 A1 | 6/2005 |
| WO | WO-9407564 A2 | 4/1994 |
| WO | WO-97/33513 | 9/1997 |
| WO | WO-03076008 A1 | 9/2003 |
| WO | WO-03082080 A3 | 10/2003 |
| WO | WO-03105658 A2 | 12/2003 |
| WO | WO-2005042091 A1 | 5/2005 |
| WO | WO-2005063332 A1 | 7/2005 |
| WO | WO-2005065771 A1 | 7/2005 |
| WO | WO-20060110338 A1 | 10/2006 |

OTHER PUBLICATIONS

Caparso, Anthony, "Systems for Selective Activation of a Nerve Trunk Using a Transvascular Reshaping Lead", U.S. Appl. No. 11/130,022, filed May 16, 2005, 33 Pgs.

Carr, William N., "Integrated Pressure Sensor With Remote Power Source and Remote Readout", i The 8th International Conference on Solid-State Sensors and Actuators and Eurosensors IX, Digest of Technical Papers, Stockholm, Sweden, (Jun. 25-29, 1995), 624-627.

Jacobsson, F., et al., "The effect of transcutaneous electric nerve stimulation in patients with therapy-resistant hypertension", *J Hum Hypertens.*, 14(12), (Dec. 2000) 795-8.

Janes, R. D., "Anatomy of human extrinsic cardiac nerves and ganglia.", *Am J Cardiol.*, 57(4) (Feb. 1, 1986), 299-309.

Libbus, Imad, "Cardiac Rhythm Management Device With Neural Sensor", U.S. Appl. No. 10/992,320, filed Nov. 18, 2004, 65 pgs.

Libbus, Imad, "Implantable Device for Treating Epilepsy and Cardiac Rhythm Disorders", U.S. Appl. No. 11/312,178, filed Dec. 21, 2005, 39 Pages.

Libbus, I., "Integrated Lead for Applying Cardiac Resynchronization Therapy and Neural Stimulation Therapy", U.S. Appl. No. 11/077,970, filed Mar. 11, 2005, 67 pgs.

Libbus, I., et al., "Method and Apparatus for Synchronizing Neural Simulation to Cardiac Cycles", U.S. Appl. No. 11/099,141, filed Apr. 5, 2005.

Libbus, Imad, "Neural Stimulation With Avoidance of Inappropriate Stimulation", U.S. Appl. No. 11/000,249, filed Nov. 30, 2004, 45 pgs.

Libbus, Imad, "Stimulator for Auricular Branch of Vagus Nerve", U.S. Appl. No. 11/005,703, filed Dec. 7, 2004, 35 pgs.

Libbus, I., et al., "System and Method for Closed-Loop Neural Stimulation", U.S. Appl. No. 10/992,319, filed Nov. 18, 2004.

Libbus, Imad, "System to Provide Myocardial and Neural Stimulation", U.S. Appl. No. 11/087,935, filed Mar. 23, 2005, 52 pgs.

Moffitt, Julia, "Combined Neural Stimulation and Cardiac Resynchronization Therapy", U.S. Appl. No. 11/078,460, filed Mar. 11, 2005, 35 pgs.

Moffitt, Julia , "Transvascular Neural Stimulation Device", U.S. Appl. No. 11/103,245, filed Apr. 11, 2005, 33 pgs.

Schauerte, P., "Ventricular rate control during atrial fibrillation by cardiac parasympathetic nerve stimulation: a transvenous approach", *Journal of the American College of Cardiology*, 34(7), (Dec. 1999), 2043-50.

Scherlag, M. A., "Endovascular Neural Stimulation Via a Novel Basket Electrode Catheter: Comparison of Electrode Configurations", *Journal of Interventional Cardiac Electrophysiology*, 4(1), (Apr. 2000), 219-224.

Scherlag, B. J., "Endovascular stimulation within the left pulmonary artery to induce slowing of heart rate and paroxysmal atrial fibrillation.", *Cardiovasc Research*, 54(2), (May 2002), 470-475.

Ziaie, Babak, "A Single-Channel Implantable Microstimulator for Functional Neuromuscular Stimulation", *IEEE Transactions on Biomedical Engineering*, 44, (Oct. 1997), 909-920.

\* cited by examiner

IMPLANTABLE AND RECHARGEABLE NEURAL STIMULATOR

TECHNICAL FIELD

This application relates generally to implantable medical devices and, more particularly, to implantable and rechargeable neural stimulators.

BACKGROUND

The automatic nervous system (ANS) regulates "involuntary" organs. The ANS includes the sympathetic nervous system and the parasympathetic nervous system. The sympathetic nervous system is affiliated with stress and the "fight or flight response" to emergencies. The parasympathetic nervous system is affiliated with relaxation and the "rest and digest response." The ANS maintains normal internal function and works with the somatic nervous system. Autonomic balance reflects the relationship between parasympathetic and sympathetic activity. A change in autonomic balance is reflected in changes in heart rate, heart rhythm, contractility, remodeling, inflammation and blood pressure. Changes in autonomic balance can also be seen in other physiological changes, such as changes in abdominal pain, appetite, stamina, emotions, personality, muscle tone, sleep, and allergies, for example.

Neural stimulation therapy has been proposed for a variety of reasons. Reduced autonomic balance (increase in sympathetic and decrease in parasympathetic cardiac tone) during heart failure has been shown to be associated with left ventricular dysfunction and increased mortality. Research also indicates that increasing parasympathetic tone and reducing sympathetic tone may protect the myocardium from further remodeling and predisposition to fatal arrhythmias following myocardial infarction. Direct stimulation of the vagal parasympathetic fibers has been shown to reduce heart rate via the sympathetic nervous system. In addition, some research indicates that chronic stimulation of the vagus nerve may be of protective myocardial benefit following cardiac ischemic insult. Neural stimulation also has been proposed to alleviate pain and as a therapy for hypertension.

It can be difficult to anticipate the amount of energy needed for neural stimulation. For effective therapy, it may be necessary to stimulate neural targets intermittently or continuously. Also, high current levels may be effective for a larger area, or lower levels may be effective for a smaller area. A flexible power management system is needed to improve neural stimulation devices.

SUMMARY

One aspect of the present subject matter relates to an implantable medical device. An embodiment of the device comprises a rechargeable power supply adapted to be recharged through an ultrasound signal, a neural stimulator connected to the rechargeable power supply, and a controller connected to the rechargeable power supply. The neural stimulator is adapted to generate a neural stimulation signal for delivery to a neural stimulation target through an electrode. The controller is further connected to the neural stimulator to control the neural stimulator according to a neural stimulation protocol. Other aspects are provided herein.

An embodiment of the implantable medical device comprises a structure, a rechargeable battery connected to the structure, a transducer adapted to charge the rechargeable battery using ultrasound energy, a sensor electrically connected to the rechargeable battery, a neural stimulator electrically connected to the rechargeable battery, and a controller electrically connected to the rechargeable battery and adapted to communicate with the sensor and the neural stimulator. The structure is selected from a group of structures consisting of: a structure adapted to be chronically implanted within a vessel, and a structure adapted to be subcutaneously implanted using a hypodermic needle.

One aspect of the present subject matter relates to a system. An embodiment of the system comprises at least two implantable medical devices, where each device being adapted to be chronically implanted into a vessel. Each device includes a rechargeable battery and an ultrasound transducer connected to the battery and adapted to recharge the battery using an ultrasound signal, a neural stimulator adapted to be powered by the battery, a sensor adapted to be powered by the battery, a controller electrically connected to a neural stimulator and the pressure sensor, and a communication module adapted to be powered by the battery and to transmit and receive ultrasound communication signals to another implantable medical device.

One aspect of the present subject matter relates to a method of operating an implantable medical device with a pressure sensor and a neural stimulator chronically implanted in a vessel. According to an embodiment of the method, a pressure is sensed within the vessel using the pressure sensor, a neural target is stimulated using the neural stimulator, a power supply is recharged using ultrasound signals.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Embodiments of the present subject matter provide implantable and rechargeable neural stimulators. Ultrasound energy can be used to recharge the stimulators. Some embodiments integrate a stimulator and a sensor in an implantable device, such that the device can autonomously provide stimulation therapy based on need. For example, a neural stimulator integrated with a pressure sensor can be activated when the sensor senses a higher blood pressure in the vasculature. The pressure sensor can use micro-electrical mechanical systems (MEMS) technology, for example. The devices can be implanted either subcutaneously or in the vasculature depending in the sensor-stimulator pair application. Examples of integrated sensors include sensors that can sense either electrical or physical physiologic parameters. These sensors can provide localized feedback for the neural stimulation. For example, a pressure sensor can sense high blood pressure and the stimulator can stimulate the appropriate nerve to lower the blood pressure. Such a system can be integrated into a device with a small form factor with its own power supply, such that the device is physically capable of being implanted through a hypodermic needle or intravascularly fed into a vessel, for example. A stent-like anchoring mechanism can be used in vasculature.

Embodiments also have the ability to wirelessly communicate other device(s), either inside or outside the body. Typically, such a system can communicate with another device within the body using ultrasound, which has minimal loss within the body. Communications with external devices can be performed using ultrasound, or inductive or RF telemetry. The intra-body communication allows the neural stimulation therapy to be to be coordinated with other implantable neural stimulators or other implantable devices such as from a cardiac rhythm management (CRM) device (e.g. pacemaker) also has such communication capability. Intrabody communication can significantly improve the efficacy of the neural stimulator, and the neural stimulation therapy.

The neural stimulator with integrated sensor can be chronically implanted to treat conditions such as hypertension and chronic pain. Some device embodiments have its own power source, and some device embodiments are powered remotely. Diagnostic and therapy functions can be performed at fixed times or based at least in part on feedback received from the sensor.

Physiology

Neural stimulation can be used to provide therapy for a variety of systemic abnormalities like hypertension. Hypertension is a cause of heart disease and other related cardiac co-morbidities. Hypertension occurs when blood vessels constrict. As a result, the heart works harder to maintain flow at a higher blood pressure, which can contribute to heart failure. A large segment of the general population, as well as a large segment of patients implanted with pacemakers or defibrillators, suffer from hypertension. The long term mortality as well as the quality of life can be improved for this population if blood pressure and hypertension can be reduced. Many patients who suffer from hypertension do not respond to treatment, such as treatments related to lifestyle changes and hypertension drugs. Hypertension generally relates to high blood pressure, such as a transitory or sustained elevation of systemic arterial blood pressure to a level that is likely to induce cardiovascular damage or other adverse consequences. Hypertension has been arbitrarily defined as a systolic blood pressure above 140 mm Hg or a diastolic blood pressure above 90 mm Hg. Hypertension occurs when blood vessels constrict. As a result, the heart works harder to maintain flow at a higher blood pressure. Consequences of uncontrolled hypertension include, but are not limited to, retinal vascular disease and stroke, left ventricular hypertrophy and failure, myocardial infarction, dissecting aneurysm, and renovascular disease.

The automatic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes, but is not limited to, the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system.

The heart rate and force is increased when the sympathetic nervous system is stimulated, and is decreased when the sympathetic nervous system is inhibited (the parasympathetic nervous system is stimulated). An afferent nerve conveys impulses toward a nerve center, such as a vasomotor center which relates to nerves that dilate and constrict blood vessels to control the size of the blood vessels. An efferent nerve conveys impulses away from a nerve center.

A pressoreceptive region or field is capable of sensing changes in pressure, such as changes in blood pressure. Pressoreceptor regions are referred to herein as baroreceptors, which generally include any sensors of pressure changes. The baroreflex functions as a negative feedback system, and relates to a reflex mechanism triggered by stimulation of a baroreceptor. Increased pressure stretches blood vessels, which in turn activates baroreceptors in the vessel walls. Activation of baroreceptors naturally occurs through internal pressure and stretching of the arterial wall, causing baroreflex inhibition of sympathetic nerve activity (SNA) and a reduction in systemic arterial pressure. An increase in baroreceptor activity induces a reduction of SNA, which reduces blood pressure by decreasing peripheral vascular resistance.

Direct electrical stimulation has been applied to the vagal nerve and carotid sinus. Research has indicated that electrical stimulation of the carotid sinus nerve can result in reduction of experimental hypertension, and that direct electrical stimulation to the pressoreceptive regions of the carotid sinus itself brings about reflex reduction in experimental hypertension.

Stimulating the sympathetic and parasympathetic nervous systems can have effects other than heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intention, increases urine secretion, and contracts the wall and relaxes the sphincter of the bladder. The functions associated with the sympathetic and parasympathetic nervous systems are many and can be complexly integrated with each other. Thus, an indiscriminate stimulation of the sympathetic and/or parasympathetic nervous systems to achieve a desired response, such as vasodilation, in one physiological system may also result in an undesired response in other physiological systems. Aspects of the present subject matter provide implantable medical devices with a form factor (physical size and shape) adapted for minimally-intrusive implantation that allows the devices to be positioned to specifically stimulate desired nerves.

The baroreflex is a reflex triggered by stimulation of a baroreceptor. A baroreceptor includes any sensor of pressure changes, such as sensory nerve endings in the wall of the auricles of the heart, cardiac fat pads, vena cava, aortic arch and carotid sinus, that is sensitive to stretching of the wall resulting from increased pressure from within, and that functions as the receptor of the central reflex mechanism that tends to reduce that pressure. A baroreflex response can be induced by stimulating some afferent nerve trunks, such as the vagus, aortic and carotid nerves, leading from the sensory nerve endings. Stimulating a baroreflex inhibits sympathetic nerve activity (stimulates the parasympathetic nervous system) and reduces systemic arterial pressure by decreasing peripheral vascular resistance and cardiac contractility.

Some aspects of the present subject matter locally stimulate specific nerve endings, such as nerve endings near or by arterial walls, rather than stimulate afferent nerve trunks in an effort to stimulate a desire response (e.g. reduced hypertension) while reducing the undesired effects of indiscriminate stimulation of the nervous system. For example, some embodiments stimulate baroreceptor sites in the pulmonary artery. Some embodiments of the present subject matter involve stimulating either baroreceptor sites or nerve endings in the aorta, the carotid sinus, the chambers of the heart, the fat pads of the heart, and some embodiments of the present subject matter involve stimulating an afferent nerve trunk, such as the vagus, carotid and aortic nerves, and various branches of these nerves such as a cardiac branch of the vagus nerve. Some embodiments stimulate afferent nerve trunks using an intravascularly placed electrode positioned in a blood vessel proximate to the nerve, such that the electrical stimulation transvascularly passes through the vessel wall to stimulate the nerve trunk.

Neural stimulation has been proposed to provide remodeling therapy to reverse the stiffening process caused by hypertension, and to provide a therapy for myocardial infarction to reduce or prevent myocardial damage caused by highly stressed regions of the heart. With respect to remodeling, the slow and progressive lowering of blood pressure enables the slower reversion of the stiffening process through the reverse remodeling. Blood pressure is reduced without compromising cardiac output in the process, thus avoiding undesired patient symptoms. With respect to myocardial infarction therapy, it is noted that an increased baroreflex stimulation compensates for reduced baroreflex sensitivity through quick vasodilation and associated decrease in systemic blood pressure, and improves the clinical outcome in patients following a myocardial infarction.

Neural stimulation can also be used to stimulate sensory nerves to block pain signals from reaching the brain. The stimulation can stimulate production of endorphins, which are chemicals produced in the brain, often in response to stress and pain, that reduce pain perception. In addition to blocking neural signals to block pain, the neural stimulation can be used to block or stimulate other neural pathways, such as to prevent or stimulate a particular muscle contraction.

Device Embodiments

Figure 1:
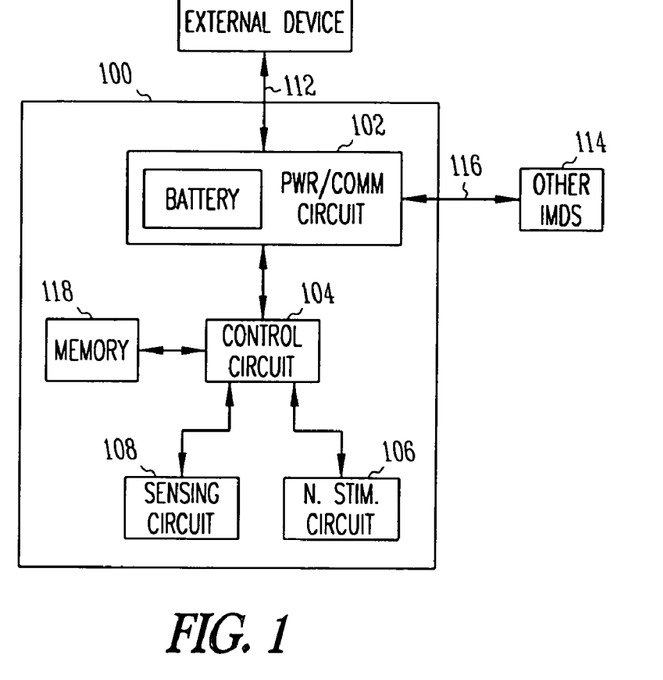
FIG. 1 is a block diagram of one embodiment of a chronically-implanted device.

FIG. 1 is a block diagram of one embodiment of a chronically-implanted device. According to this embodiment, the chronically-implanted device 100 forms an intravascular neural stimulator and sensor that includes a power/communication circuit 102, a control circuit 104, a neural stimulation circuit 106, and a sensing circuit 108. The components of the chronically-implanted device 100 will be described in more detail below. The neural stimulation circuit 106 functions as a therapy-providing circuit which is operative to provide the desired therapy, such as neural stimulation therapy to treat hypertension and neural stimulation therapy to alleviate pain. In an embodiment, the sensing circuit 108 is operative to sense pressure.

The illustrated power and communication circuitry 102 includes a rechargeable battery, which is capable of being recharged using ultrasound signals. In the embodiment of FIG. 1, the power and communication circuitry 102 are combined into one box to illustrate that they are capable of being integrated. Alternatively, the power circuitry and communication circuitry are capable of being separate circuits. With respect to an integrated power/communication circuit, data is capable of being encoded into the power transmission as a modulation of the power signal. As such, one embodiment of the chronically-implanted device 100 provides a combined power/communication link 112 between the power/communication circuit 102 and the external device 110. Also with respect to an integrated power/communication circuit, some embodiments share sub-components such as ultrasound transducer(s). Another embodiment of the chronically-implanted device 100 provides a power link and a separate communication link between the power/communication circuit 102 and the external device 110. One embodiment of the chronically-implanted device 100 provides wireless (e.g. ultrasound), combined power/communication link. Furthermore, with respect to device embodiments that include separate power and communication links, the power link is capable of being wireless (e.g. ultrasound), and the communication link is independently capable of being wireless (e.g. ultrasound). For example, the circuit 102 in the illustrated device can include a transceiver and associated circuitry for use to communicate with a programmer or another external or internal device. Various embodiments have wireless communication capabilities. For example, some transceiver embodiments use a telemetry coil to wirelessly communicate with a programmer or another external or internal device. Some communication modules have transducers for use to communicate through ultrasound signals.

According to one embodiment, the chronically-implanted device is an intravascular device. For example, one device embodiment has the form of a stent or a stent-like device. Some device embodiments communicate to other implantable medical devices 114 using communication link 116. Some embodiments use an ultrasound communication link 116. According to various embodiments, the device functions as a satellite and communicates to a planet by way of ultrasound energy.

According to one embodiment, the chronically-implanted device includes control circuitry 104 to control the functions of one or more of the subsystems or components shown in FIG. 1. According to various embodiments, the chronically-implanted device employs a dedicated controller to monitor, to control, or to monitor and control the functions of any or all of the components. According to various embodiments, the controller is adapted to trigger the sensing circuit, the stimulating circuit, or the sensing and stimulating circuits. According to one embodiment, the controller is used to manage system power by controlling power flow between the power circuitry and other system components. The controller is capable of controlling the operation of any system component, and of providing the system clock for electronics timing and functionality. According to one embodiment, the controller is a state machine. The illustrated device includes controller circuitry 104 and a memory 118. The controller circuitry is capable of being implemented using hardware, software, and combinations of hardware and software. For example, according to various embodiments, the controller circuitry includes a processor to perform instructions embedded in the memory to perform functions associated with NS therapy such as AHT therapy. The illustrated IMD is adapted to perform neural stimulation functions. Some embodiments of the illustrated IMD performs an anti-hypertension (AHT) function.

The illustrated device further includes neural stimulation circuitry 106. Various embodiments of the device also includes sensor circuitry 108. The neural stimulation circuitry is used to apply electrical stimulation pulses to desired neural target sites, such as baroreceptor sites in the pulmonary artery, through one or more stimulation electrodes. In various embodiments, at least one electrode is connected to the neural stimulation circuitry using a lead such that the neural stimulation circuitry applies electrical stimulation through the lead and electrode. In various embodiments, at least one electrode is wirelessly coupled to the neural stimulation circuitry such that the neural stimulation circuitry wirelessly applies electrical stimulation to the electrode. Such wireless embodiments provide additional flexibility in placement of the electrode(s) and device. In various embodiments, at least one electrode is integrated with or otherwise formed on the housing of the device such that the neural stimulation circuitry applies electrical stimulation through the electrode on the housing. The sensor circuitry can be used to provide feedback for the neural stimulation. For example, the sensing circuit 108 can be used to detect and process ANS nerve activity and/or surrogate parameters such as blood pressure, respiration and the like, to determine the ANS activity.

According to various embodiments, the stimulator circuitry 106 includes modules to set any one or any combination of two or more of the following pulse features: the amplitude of the stimulation pulse, the frequency of the stimulation pulse, the burst frequency or duty cycle of the pulse, and the wave morphology of the pulse. Examples of wave morphology include a square wave, triangle wave, sinusoidal wave, and waves with desired harmonic components to mimic white noise such as is indicative of naturally-occurring baroreflex stimulation.

Various implantable neural stimulator embodiments include an integrated pressure sensor (IPS), to monitor changes in blood pressure, for example. Thus, the sensor monitors the effect of the neural stimulation. In various embodiments, for example, micro-electrical mechanical systems (MEMS) technology is used to sense the blood pressure. Some sensor embodiments determine blood pressure based on a displacement of a membrane. The stimulator and sensor functions can be integrated, even if the stimulator and sensors are located in separate devices.

This device, for example, is capable of being intravascularly introduced or subcutaneously introduced by a hypodermic needle to stimulate a neural target, such as the baroreceptor sites in the pulmonary artery, the aortic arch, the ligamentum arteriosum, the coronary sinus, and the atrial and ventricular chambers, and neural targets such as the cardiac fat pads.

Thus, various embodiments of the present subject matter provide an implantable neural stimulation device that automatically modulates neural stimulation using an IPS based, at least in part, on localized feedback from the integrated pressure sensor. This localized sensing improves feedback control. According to various embodiments, the device monitors pressure parameters such as mean arterial pressure, systolic pressure, diastolic pressure and the like. As mean arterial pressure increases or remains above a programmable target pressure, for example, the device stimulates the baroreflex at an increased rate to reduce blood pressure and control hypertension. As mean arterial pressure decreases towards the target pressure, the device responds by reducing the stimulation of the baroreflex. In various embodiments, the algorithm takes into account the current metabolic state (cardiac demand) and adjusts neural stimulation accordingly. A neural stimulation device having an IPS is able to automatically modulate neural stimulation, which allows an implantable NS device to determine the level of hypertension in the patient and respond by delivering the appropriate level of therapy.

An aspect of the present subject matter relates to a chronically-implanted stimulation device specially designed to treat hypertension by monitoring blood pressure and stimulating baroreceptors to activate the baroreflex and inhibit sympathetic discharge from the vasomotor center. Baroreceptors are located in various anatomical locations such as the carotid sinus and the aortic arch. Other baroreceptor locations include the pulmonary artery, including the ligamentum arteriosum, and sites in the atrial and ventricular chambers. In various embodiments, the neural stimulation device is integrated into a pacemaker/defibrillator or other electrical stimulator system. Components of the system include a pulse generator, sensors to monitor blood pressure or other pertinent physiological parameters, electrodes to apply electrical stimulation to neural targets, algorithms operated on by a controller to determine the when and how to administer stimulation, and algorithms operated on by the controller to manipulate data for display and patient management. The controller is adapted to control the neural stimulator to provide a neural stimulation therapy using feedback from the pressure sensor. According to various embodiments, the therapy includes one or more of a treatment following myocardial infarction, a treatment to alleviate pain, and a therapy for hypertension. As those of ordinary skill in the art will understand upon reading and comprehending this disclosure, other neural stimulation therapies can be performed.

A system according to these embodiments can be used to augment partially successful treatment strategies. As an example, undesired side effects may limit the use of some pharmaceutical agents. The combination of a system according to these embodiments with reduced drug doses may be particularly beneficial.

Form Factor (Size/Shape)

According to one embodiment, the electrical stimulation functions provided by the intravascular device involves only a minimally invasive surgery, even when several electrodes are placed for multisite pacing. Strategies that incorporate multisite pacing are believed to offer therapeutic advantages.

Figure 2:
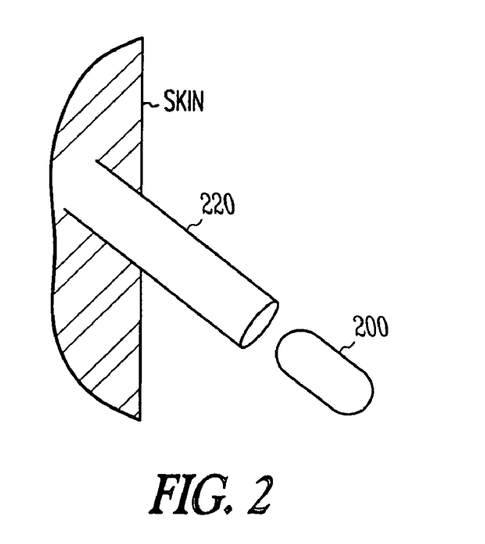
FIG. 2 illustrates an embodiment where the device implanted subcutaneously using a hypodermic needle.

FIG. 2 illustrates the device 200 implanted subcutaneously using a hypodermic needle 220. One embodiment of the chronically-implanted device is an intravascular device. One intravascular device embodiment has a structure of a stent for preventing restenosis. For example, in the embodiment in which the chronically-implanted device has a stent-like form, the structure of the expanded device exerts a pressure on vascular walls to prevent restenosis. Additionally, various embodiments of the chronically-implanted device includes appropriate sensors for monitoring mechanical/fluid properties such as the hemodynamic properties of blood flow and pressure. The sensing function is described in more detail below. Embodiments of the stent-like, chronically-implanted device include balloon-expandable stents and self-expanding stents. The expanded stent applies pressure against the interior of the vessel to widen the vessel. The catheter is removed, leaving the expanded stent securely in place. Furthermore, one embodiment of the chronically-implanted device has the structure of and performs the mechanical function of a vascular occlusion device.

Figure 3:
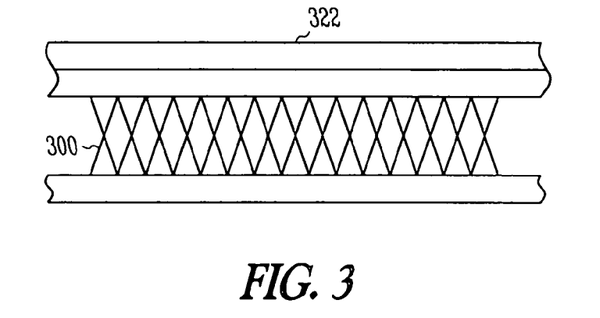
FIG. 3 illustrates an embodiment where a chronically-implanted device, in the form of a stent, is placed within a vessel and where the device includes an encapsulated electronics platform.

FIG. 3 illustrates a chronically-implanted device 300 in the form of a stent placed within a vessel 322 in which the device includes an encapsulated electronics platform. Intelligent functions, in addition to the mechanical function of preventing restenosis, are capable of being performed by the stent because of circuitry, or microsystems, contained on the electronics platform.

The chronically-implanted device diminishes problems associated with invasive surgical procedures because the device is small and is capable of being placed by a hypodermic needle or a catheter, for example, into position through the vascular network or through the lumen of other canals or tubular structures of a biosystem.

According to various embodiments, the chronically-implanted device of the present subject matter may be formed to function as a variety of stents. These stents include, but are not limited to, a coronary stent, a vascular stent, a tracheobronchial stent, a colonic/duodenal stent, an esophageal stent, a biliary stent, a urological stent, a neurovascular stent, an abdominal aortic aneurysm stent, a renal stent, and a carotid stent.

Figure 4:
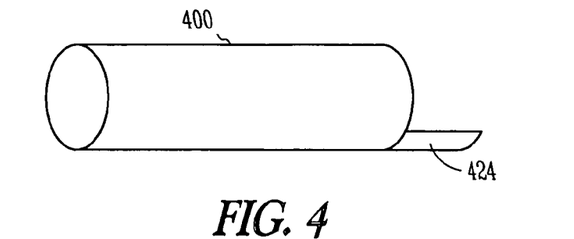
FIG. 4 illustrates one embodiment of a chronically-implanted device in the form of a stent that includes an encapsulated electronics platform.
Figure 5:
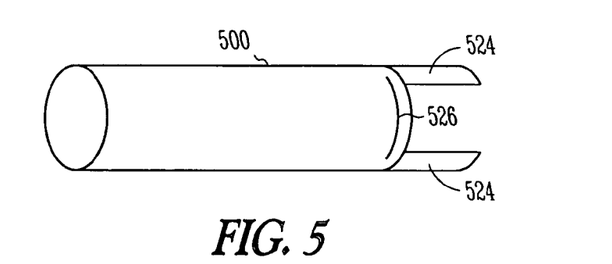
FIG. 5 illustrates one embodiment of a chronically-implanted device in the form of a stent that includes two encapsulated electronics platforms.

FIG. 4 illustrates one embodiment of a chronically-implanted device 400 in the form of a stent that includes an encapsulated electronics platform 424. The electronics platform 424 includes the circuitry from the various embodiments previously shown and described with respect to FIG. 1. FIG. 5 illustrates one embodiment of a chronically-implanted device 500 in the form of a stent that includes two encapsulated electronics platforms 524. Additional electronic platforms may be incorporated as desired. One embodiment of the device includes at least one dedicated electrical connector that couples two or more electronics platforms. One embodiment of the device uses an insulated strand of mesh 526 from the stent structure to couple two or more electronics platforms.

The stent-like structure of one embodiment of a chronically-implanted device includes at least two conducting portions separated by an insulator. One of the conducting portions functions as an anode and another functions as a cathode. These conducting portions are used, according to various embodiments of the chronically-implanted device, to provide electrical therapy (e.g. neural stimulation), to receive power transmissions, and/or to receive and transmit communication transmissions.

Figure 6:
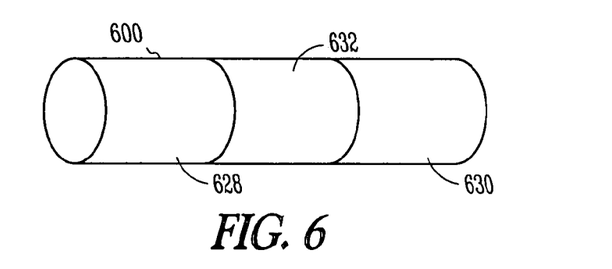
FIG. 6 illustrates an embodiment of a chronically-implanted device having a cylindrical or radially-oriented anode and cathode.
Figure 7:
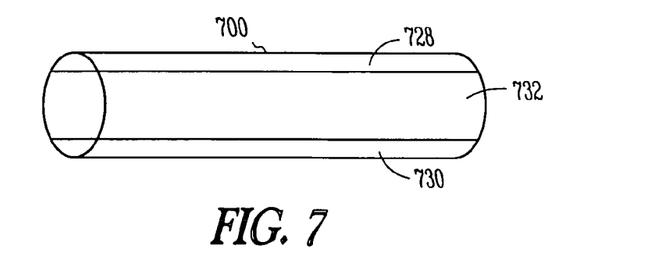
FIG. 7 illustrates an embodiment of a chronically-implanted device having a longitudinally-oriented anode and cathode.

FIG. 6 illustrates one embodiment of a chronically-implanted device 600 having a cylindrical or radially-oriented anode 628 and cathode 630. FIG. 7 illustrates one embodiment of a chronically-implanted device 700 having a longitudinally-oriented anode 728 and cathode 730. According to various embodiments, these split stent-like structures are formed from a conventional stent. The conventional stent is cut as required to form or isolate a radially-oriented anode and cathode or a longitudinally-oriented anode and cathode. The anode and cathode are recombined using an insulator material 632 or 732.

Rechargeable Power Supply

Figure 8:
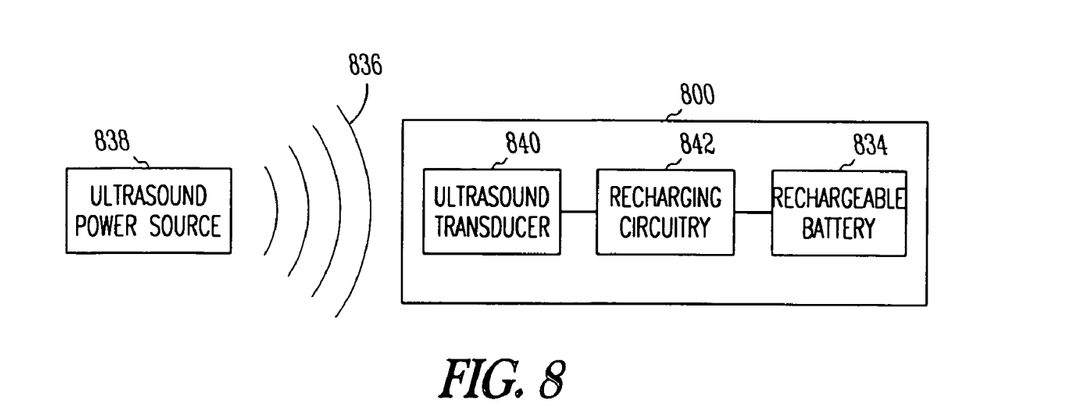
FIG. 8 illustrates an embodiment where the chronically-implanted device is powered by a small rechargeable battery adapted to be recharged using ultrasound waves from an ultrasound power source.

The chronically-implanted device includes power circuitry. According to various embodiments, for example, the power circuitry forms part of the power/communication circuit 102 of FIG. 1. As illustrated in FIG. 8, some embodiments of the chronically-implanted device is powered by a small rechargeable battery adapted to be recharged using ultrasound waves 836 from an ultrasound power source 838. The use of ultrasound allows the device to be recharged remotely. The illustrated device 800 includes an ultrasound transducer 840, or an array of transducers, to convert the ultrasound signals into an electrical signal. Examples of ultrasonic transducers include an acoustic, piezoelectric, electrostatic, and magnetostrictive devices. Recharging circuitry 842 is connected to receive the electrical signal from the transducer and process the signal to charge to battery 834.

Communication

Figure 9:
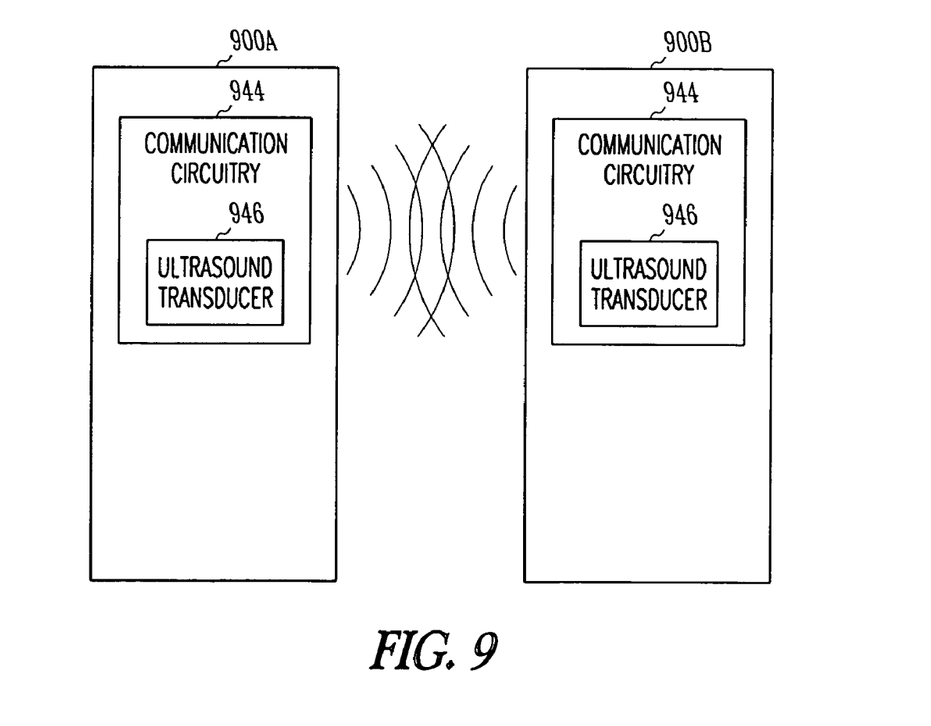
FIG. 9 illustrates a system embodiment where two implantable neural stimulation devices are adapted to communicate with each other.

The chronically-implanted device includes communication circuitry used to communicate to an external device. According to various embodiments, for example, the communication circuitry forms part of the power/communication circuits 102 of FIG. 1. Embodiments provide communication between the chronically-implanted device and the external device using ultrasound waves, for example. As illustrated in FIG. 9, two implantable neural stimulation devices 900A and 900B are adapted to communicate with each other. Each device has communication circuitry 944 with an ultrasound transducer 946 for receiving and generating an ultrasound signal. The communication circuitry is adapted to process the signals into information understandable by the device.

Neural Stimulator

According to one embodiment, the neural stimulator has adjustable stimulation parameters such as pulse width, frequency, duty cycle, burst duration, amplitude, stimulation modes (bi-polar or uni-polar, for example), and stimulation site if multiple sites are available. According to one embodiment, the neural stimulation circuitry receives its parameters from the controller.

The device includes electrode(s) to provide neural stimulation. Some device embodiments sense electrical signals with electrode(s). Some electrode embodiments are connected to the device by a lead or tether. In some embodiments, the electrode is attached to the device housing; and in some embodiments, the electrode forms at least part of the device housing.

Electrode embodiments include intravascularly-placed electrodes and electrodes placed subcutaneously. With respect to intravascularly-placed embodiments, at least one an electrode is placed in a blood vessel and positioned to transvascularly stimulate a nerve on or near the extravascular surface of the vessel. Transvascular stimulation avoids direct contact with nerves during stimulation and reduces problems associated with neural inflammation or injury induced by direct stimulation. Transvascular stimulation using intravascularly-fed leads provides relatively non-invasive access to anatomical targets and points of innervation.

In an example, the expandable electrode includes a mesh, at least part of which is electrically conductive. In an example, the expandable electrode is formed from Platinum or Platinum-Iridium. In an embodiment, the expandable electrode is similar to a stent. A nerve trunk extends on or near an extravascular surface of the blood vessel. An expandable electrode can be implanted at or near a location in the blood vessel where the nerve trunk crosses the blood vessel. In an example, the expandable electrode transmits neural stimulation energy through a predetermined surface area of the wall of a blood vessel. In an example, the expandable electrode has a length that provides enough surface area that there is at least some flexibility in the placement of the expandable electrode in the vessel with respect to the target nerve. In an example, the length of the expandable electrode is about 0.5 to 2.0 cm.

In an embodiment, the entire surface area of the expandable electrode that touches the blood vessel wall is conductive. In an embodiment, at least a part of the surface area of the electrode is non-conductive. For example, an electrode can be formed and positioned to deliver stimulation to through a conductive part of the electrode to a portion of a blood vessel that is proximate a nerve. The expandable electrode has an expanded diameter that is sized for implantation in a blood vessel of a particular size range. In one example, where the electrode is size for implantation in the internal jugular vein, the expanded diameter is about 0.5 to 1.5 cm, and the length of the electrode is about 1.0 cm.

In an example, the expandable electrode is covered with a drug, such as a drug that prevents occlusion, or a drug that reduces inflammation of the blood vessel near the electrode. The expandable electrode is coupled to a power source that delivers an electrical stimulation. The electrode can be coupled to the power source through a lead, or the electrode can form at least part of a device structure that contains the power source.

The electrode(s) may be implanted in various locations in the body, including a variety of locations near a trunk or branch of a sympathetic or parasympathetic nerve system. In an example, the electrode transvascularly stimulates a peripheral nerve trunk. Examples of a peripheral nerve trunk include the vagus nerve, aortic nerve, and carotid sinus nerve. In another example, the electrode stimulates a nerve branch, such as a vagal cardiac branch. The electrode(s) can be implanted in various vessels or chambers such as the superior vena cava (SVC) to transvascularly stimulate a nerve or nerve trunk on or near the SVC, and a coronary sinus.

Electrodes can be implanted within the atria, the ventricle, superior vena cava, inferior vena cava, aorta, right pulmonary veins, and right pulmonary artery, and coronary sinus. An electrode can be implanted in one or more of the blood vessels listed above at a location where a nerve, nerve branch, or nerve trunk passes an extravascular surface of the blood vessel. The implanted electrode transvascularly stimulates a nerve, nerve branch, or nerve trunk through the blood vessel. In one example, an electrode is implanted in the SVC near a vagal nerve trunk. In another example, an electrode is implanted in the coronary sinus near a vagal nerve trunk.

In another example, a cardiac fat pad is transvascularly stimulated by an implanted electrode. A cardiac fat pad is located between the superior vena cava and aorta, a cardiac fat pad is located proximate to the right cardiac veins, and a cardiac fat pad is located proximate to the inferior vena cava and left atrium. Electrodes implanted in the superior vena cava, aorta, cardiac veins, inferior vena cava or coronary sinus can be used to stimulate various cardiac fat pads.

Electrodes can be implanted at locations in blood vessels near a vagus nerve. The right vagus nerve trunk extends near the carotid artery and subclavian artery. The left vagus nerve extends near the carotid artery and subclavian artery. Additionally, electrodes can be implanted in the carotid sinus near the carotid sinus nerve.

The left vagus nerve extends next to a subclavian artery also extends past the ligamentum arteriosum. Various nerves extend around the arch of the aorta. The anterior pulmonary plexus crosses the left pulmonary artery. The right vagus nerve extends past a subclavian artery and the cupola of pleura. Cardiac nerves extend past the brachiocephalic trunk near the trachea. Cardiac nerves also extend past the arch of an azygos vein to the right pulmonary artery. A left phrenic nerve extends past a cupola of pleura, an internal thoracic artery, and left pulmonary artery. The vagus nerve, recurrent laryngeal nerves, cardiac nerves, and the anterior pulmonary plexus extend near the left pulmonary artery and ligamentum arteriosum. An expandable electrode, such as a stent, is chronically implantable in these blood vessels to transvascularly stimulate a nerve or nerve trunk that extends on or near these blood vessel. For example, the vagus nerve can be transvascularly stimulated from the azygos vein or internal jugular vein. An afferent nerve conveys impulses toward a nerve center, and an efferent nerve conveys impulses away from a nerve center. Both afferent and efferent nerves can be stimulated transvascularly. In other examples, nerve trunks innervating other organs, such as the lungs or kidneys are transvascularly stimulated.

Sensor(s)

According to one embodiment, the sensor functions provided by the device are capable of providing continuous intravascular measurements, such as blood pressure, blood flow and vessel size. According to one embodiment, the chronically-implanted device, or system of devices, communicates with a central unit, such as an implantable device, and monitors blood flow, blood pressure, and vessel inner diameter.

According to various embodiments, Micro-Electro-Mechanical Systems (MEMS) technology is used to fabricate the required circuitry for the chronically-implanted device on silicon substrate. Currently, for example, the MEMS circuitry is between about 1 mm×3 mm for some of the present applications; however, the MEMS circuitry is capable of being otherwise sized. MEMS devices have been used in catheter-based systems to measure intracardiac pressure and temperature.

In general, a MEMS device contains micro-circuitry on a tiny silicon chip into which some mechanical device such as a sensor has been manufactured. These chips are able to be built in large quantities at low cost, making the MEMS device cost-effective. MEMS technology integrates mechanical elements, sensors, actuators, and electronics on a common silicon substrate using microfabrication technology. MEMS combines silicon-based microelectronics with microsensors and microactuators to provide a complete system on a chip. The micromechanical components are fabricated using micromachining processes that are compatible with the integrated circuit process sequences. Parts of the silicon wafer are selectively etched away or new structural layers are added to form the mechanical and electromechanical devices. According to various embodiments of the chronically-implanted device, at least one of the components (i.e. the power circuitry, the communication circuitry, the control circuitry, the stimulation circuitry, and the sensing circuitry) are integrated onto silicon MEMS technology to reduce size.

Examples of pressure sensors include capacitive membrane and piezoelectric sensors. According to various embodiments, the capacitive membrane sensor is used to measure pressure within the vessel wall, to derive flow, to derive rate, to monitor cardiac output, to monitor hemodynamic stability, and to monitor Electro-Mechanical Dissociation (EMD). It was stated earlier in the background that there is a correlation between cardiac electrical abnormalities and coronary vascular abnormalities. However, it is possible that the electrical functions appear normal but the mechanical functions are abnormal, or that the mechanical functions are normal but the electrical functions appear abnormal. EMD identifies conditions in which electrical and mechanical functions of the biological system are not in accord or agreement with each other.

According to various embodiments, the piezoresistive sensor is used to measure pressure within the vessel wall, to derive flow, to derive rate, to monitor cardiac output, to monitor hemodynamic stability, and to monitor EMD. In one embodiment the piezoresistive sensor is used to measure contraction strength of the heart.

System Embodiments

Figure 10:
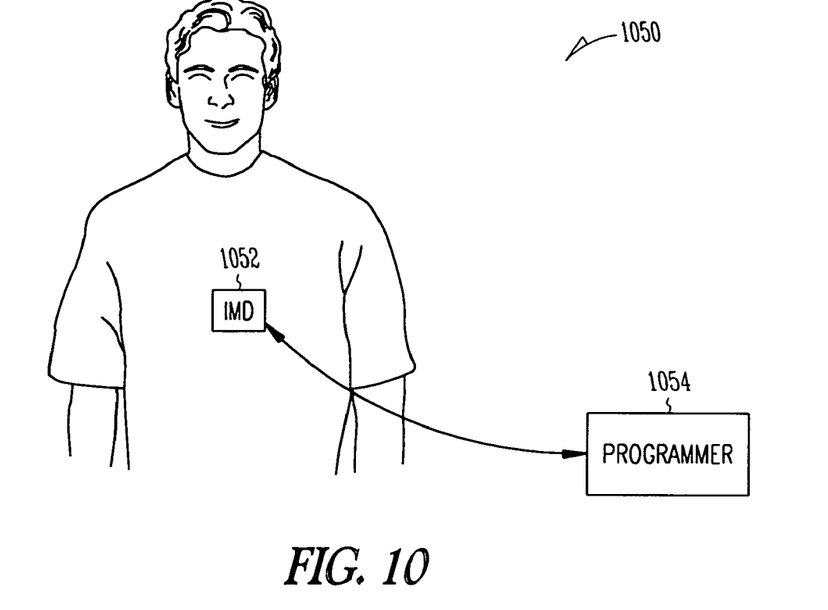
FIG. 10 illustrates a system including an implantable medical device (IMD) and a programmer, according to various embodiments of the present subject matter.

FIG. 10 illustrates a system 1050 including an implantable medical device (IMD) 1052 and a programmer 1054, according to various embodiments of the present subject matter. Various embodiments of the IMD 1052 include neural stimulator functions only, and various embodiments include a combination of NS and CRM functions. The programmer 1054 and the IMD 1052 are capable of wirelessly communicating data and instructions. In various embodiments, for example, the programmer and IMD use telemetry coils to wirelessly communicate data and instructions. Some embodiments use ultrasound transducers for communications, and some embodiments use ultrasound transducers to recharge the IMD. Thus, the programmer can be used to adjust the programmed therapy provided by the IMD, and the IMD can report device data (such as battery data and lead resistance) and therapy data (such as sense and stimulation data) to the programmer using radio telemetry, for example. According to various embodiments, the IMD stimulates baroreceptors to provide NS therapy such as AHT therapy. Various embodiments of the IMD stimulate neural targets using a lead fed through vasculature. Various embodiments of the IMD have a form factor conducive to subcutaneous implantation through a hypodermic needle. According to various embodiments, the IMD includes a sensor to sense ANS activity. Such a sensor can be used to perform feedback in a closed loop control system. For example, various embodiments sense surrogate parameters, such as respiration and blood pressure, indicative of ANS activity. Thus, various embodiments provide a pressure sensor to sense pressure. According to various embodiments, the IMD further includes cardiac stimulation capabilities, such as pacing and defibrillating capabilities in addition to the capabilities to stimulate baroreceptors and/or sense ANS activity.

Figure 11:
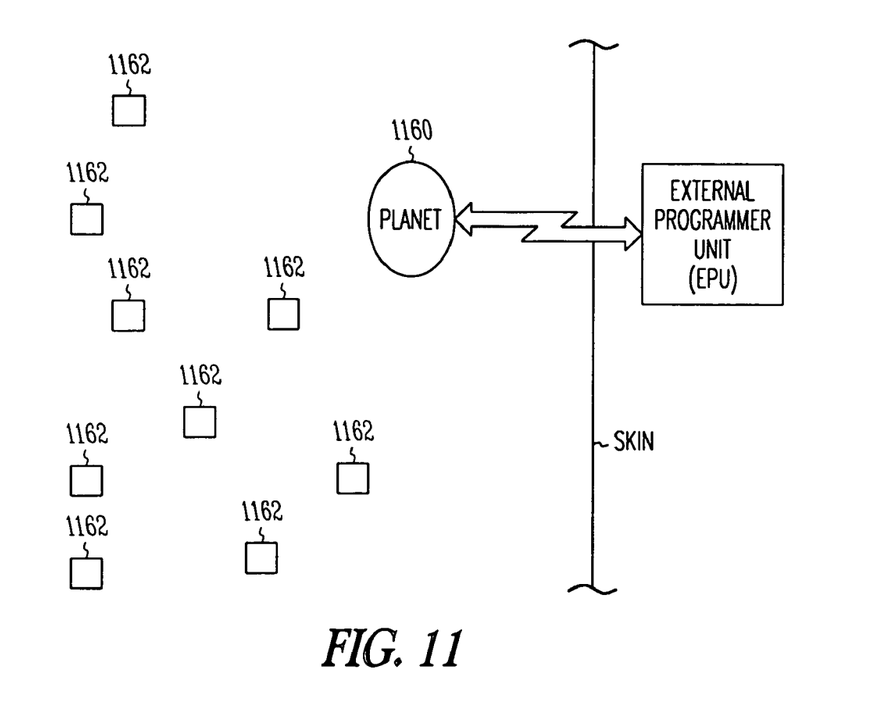
FIG. 11 illustrates an embodiment where an implantable medical device network includes a planet and a plurality of satellites formed by the chronically-implanted device.

According to one embodiment, the chronically-implanted device is incorporated as one or more satellites in a satellite-planet configuration. FIG. 11 illustrates an implantable medical device network including a planet 1160 and a plurality of satellites 1162 formed by the chronically-implanted device. The planet 1160 can be either another implantable device (e.g. cardiac rhythm management device) or an external device (e.g. programmer). The satellites are capable of being placed throughout a biosystem according the desired application.

In general, the planet is implanted or externally retained. The planet is capable of wirelessly communicating, i.e. without a direct electrical connection, to each satellite using ultrasound, for example, or is capable of being tethered to each satellite. The planet individually commands each satellite to provide sensing functions and therapy functions such as delivering electrical pulses or drugs. In another embodiment, the satellites function autonomously and are in communication with the planet. This communication is initiated by the planet and/or by the satellite in various embodiments. Additionally, each satellite is capable of determining when a sense event has occurred, along with an identifying code indicating to the planet which satellite detected the sense event. In one embodiment, the planet processes the encoded signals received from the network of satellites, assigns time values to each satellite when that satellite detects a sense event, compares the time values to a template of normal time values, and determines if a therapy should be applied. Further, the planet selects and applies the appropriate therapy for the sensed event. In various embodiments, the satellites are self-powered using a rechargeable battery capable of being recharged using ultrasound.

Therapy Examples

According to various embodiments, the therapy includes one or more of a treatment following myocardial infarction, a treatment to alleviate pain, and a therapy for hypertension.

Neural stimulation therapies can be used to treat one or more of a variety of conditions, including but not limited to arrhythmias, heart failure, syncope, or orthostatic intolerance. In an example, an efferent peripheral nerve is transvascularly stimulated by an implanted expandable electrode. In another example, an afferent peripheral nerve is stimulated.

In an example, electrical stimulation is transvascularly delivered to a parasympathetic nerve to reduce chronotropic, ionotropic, and dromotropic responses in the heart. In a therapy example, electrical stimulation is transvascularly delivered to a parasympathetic nerve trunk during heart failure. In another therapy example, electrical stimulation is transvascularly delivered to a parasympathetic nerve trunk following a myocardial infarction to protect against arrhythmias or prevent cardiac remodeling.

Transvascular stimulation of a vagus nerve trunk is used in a number of therapies. In an example, vagal nerve stimulation simultaneously increases parasympathetic tone and decreases sympathetic myocardial tone. In an example, a vagus nerve trunk is transvascularly stimulated following cardiac ischemic insult. Increased sympathetic nervous activity following ischemia often results in increased exposure of the myocardium to epinephrine and norepinephrine. These catecholamines activate intracellular pathways within the myocytes, which lead to myocardial death and fibrosis. This effect is inhibited by stimulation of the parasympathetic nerves, such as vagus nerves. In an example, vagal stimulation from the SVC lowers heart rate, overall blood pressure, and left ventricular pressure. Stimulation of the vagal cardiac nerves following myocardial infarction, or in heart failure patients, can be beneficial in preventing further remodeling and arrhythmogenesis.

In other examples, transvascular neural stimulation is used to treat other conditions such as hypertrophic cardiomyopathy (HCM) or neurogenic hypertension, where an increase parasympathetic cardiac tone and reduction in sympathetic cardiac tone is desired. In another example, a bradycardia condition is treated by transvascularly stimulating a sympathetic nerve trunk. In another example, the ionotropic state of the heart is increased by transvascularly stimulating a sympathetic nerve trunk.

Another example of a neural stimulation therapy includes Functional Electric Stimulation (FES), such as may be used in a therapy for foot drop, standing, walking, hand grasp, and shoulder control. FES can be used as a therapy for spinal cord injuries, and its debilitating effect on a variety of bodily functions. In various embodiments, electrodes used in FES therapies can be subcutaneously placed near or next to a desired nerve for the therapy. Other examples include therapies for the treatment of stroke, epilepsy, eating disorders, sleeping disorders, and pain. Various facial nerves can be stimulated to treat facial droop, migraine headaches and other headaches, for example. These therapy examples are not intended to be exclusive, as those of ordinary skill in the art will understand, upon reading and understanding this disclosure, how to apply the present subject matter for other neural stimulation therapies.

This disclosure includes several processes, circuit diagrams, and structures. The present invention is not limited to a particular process order or logical arrangement. Although specific embodiments have been illustrated and described herein, it will be appreciated by those of ordinary skill in the art that any arrangement which is calculated to achieve the same purpose may be substituted for the specific embodiments shown. This application is intended to cover adaptations or variations. It is to be understood that the above description is intended to be illustrative, and not restrictive. Combinations of the above embodiments, and other embodiments, will be apparent to those of skill in the art upon reviewing the above description. The scope of the present invention should be determined with reference to the appended claims, along with the full scope of equivalents to which such claims are entitled.

What is claimed is:

1. An implantable medical device for therapeutically stimulating a neural stimulation target of a human from a blood vessel of the human, comprising:
  a rechargeable power supply adapted to be recharged through an ultrasound signal;
  an electrode;
  a neural stimulator connected to the rechargeable power supply, the neural stimulator being adapted to generate a neural stimulation signal for delivery to the neural stimulation target through the electrode;
  a controller connected to the rechargeable power supply, and further connected to the neural stimulator to control the neural stimulator according to a neural stimulation protocol to deliver a neural stimulation therapy;
  a pressure sensor electrically connected to the controller, wherein the power supply, the electrode, the neural stimulator, the controller and the pressure sensor are adapted to be chronically implanted in the blood vessel.

2. The device of claim 1, wherein at least one of the electrode and the pressure sensor are integrated with a housing of the implantable medical device.

3. The device of claim 2, wherein both of the electrode and the pressure sensor are integrated with a housing of the implantable medical device.

4. The device of claim 1, wherein the controller is adapted to autonomously control a neural stimulation process in response to a sensed pressure within the vessel.

5. The device of claim 1, wherein the controller is adapted to control a baroreceptor stimulation process in response to a sensed pressure within the vessel.

6. The device of claim 5, wherein the controller is adapted to control a vagal stimulation process in response to the sensed pressure within the vessel.

7. The device of claim 5, wherein the controller is adapted to control neural stimulation of a cardiac nerve in response to the sensed pressure within the vessel.

8. The device of claim 1, wherein the device has a structure adapted to expand to secure the device in the vessel.

9. The device of claim 1, wherein the controller is adapted to respond to a sensed pressure within the blood vessel by activating the neural stimulator to deliver the neural stimulation therapy.

10. The device of claim 1, wherein the neural stimulation target is an afferent nerve trunk outside of the blood vessel, the electrode and the neural stimulator are adapted to cooperate to transvascularly stimulate the afferent nerve trunk from a chronically implanted position within the blood vessel to trigger a baroreflex response, and the controller is adapted to control the neural stimulator to deliver a baroreflex therapy.

11. The device of claim 1, wherein the neural stimulation target includes a baroreceptor, the electrode and the neural stimulator are adapted to cooperate to stimulate the baroreceptor from a chronically implanted position within the blood vessel to trigger a baroreflex response, and the controller is adapted to control the neural stimulator to deliver a baroreflex therapy.

12. An implantable medical device for therapeutically stimulating a neural stimulation target of a human, comprising:
  a rechargeable power supply adapted to be recharged through an ultrasound signal;
  an electrode;
  a neural stimulator connected to the rechargeable power supply, the neural stimulator being adapted to generate a neural stimulation signal for delivery to the neural stimulation target through the electrode;
  a controller connected to the rechargeable power supply, and further connected to the neural stimulator to control the neural stimulator according to a neural stimulation protocol to deliver a neural stimulation therapy; and
  a communication module connected to the controller, the communication module being adapted to transmit and receive ultrasound communication signals,
  wherein the rechargeable power supply and the communication module share subcomponents.

13. The device of claim 12, wherein the device is adapted to communicate with at least one other implantable device using ultrasound communication signals.

14. The device of claim 12, wherein the device is adapted to communicate with an external device using ultrasound communication signals.

15. The device of claim 12, wherein the rechargeable power supply and the communication module share at least one ultrasound transducer.

16. An implantable medical device for therapeutically stimulating a neural stimulation target of a human, comprising:
- a rechargeable power supply adapted to be recharged through an ultrasound signal;
- an electrode;
- a neural stimulator connected to the rechargeable power supply, the neural stimulator being adapted to generate a neural stimulation signal for delivery to the neural stimulation target through the electrode; and
- a controller connected to the rechargeable power supply, and further connected to the neural stimulator to control the neural stimulator according to a neural stimulation protocol to deliver a neural stimulation therapy,
- wherein the neural stimulation target includes a sympathetic or a parasympathetic nervous system target, and the controller is adapted to control the neural stimulator according to a neural stimulation protocol to elicit a sympathetic or parasympathetic response.

17. The device of claim 16, further comprising a sensor connected to the controller, and electrically connected to the power supply.

18. The device of claim 16, wherein the neural stimulator is adapted to deliver the neural stimulation signal through a lead to the electrode.

19. The device of claim 16, wherein the neural stimulator is adapted to wirelessly deliver the neural stimulation signal to the electrode.

20. The device of claim 16, wherein the controller is adapted to control the neural stimulator to deliver a hypertension therapy.

21. The device of claim 16, wherein the controller is adapted to control the neural stimulator to deliver a remodeling therapy.

22. An implantable medical device for therapeutically stimulating a neural stimulation target of a human, comprising:
- a rechargeable power supply adapted to be recharged through an ultrasound signal;
- an electrode;
- a neural stimulator connected to the rechargeable power supply, the neural stimulator being adapted to generate a neural stimulation signal for delivery to the neural stimulation target through the electrode; and
- a controller connected to the rechargeable power supply, and further connected to the neural stimulator to control the neural stimulator according to a neural stimulation protocol to deliver a neural stimulation therapy,
- wherein the neural stimulation target includes sensory nerves that, when stimulated, block pain signals from reaching a brain of the human, and the controller is adapted to control the neural stimulator to deliver a therapy to alleviate pain.

23. An implantable medical device for therapeutically stimulating a neural stimulation target of a human, comprising:
- a rechargeable power supply adapted to be recharged through an ultrasound signal;
- an electrode;
- a neural stimulator connected to the rechargeable power supply, the neural stimulator being adapted to generate a neural stimulation signal for delivery to the neural stimulation target through the electrode; and
- a controller connected to the rechargeable power supply, and further connected to the neural stimulator to control the neural stimulator according to a neural stimulation protocol to deliver a neural stimulation therapy,
- wherein the neural stimulation target includes a nerve for a particular muscle of a human that, when stimulated, stimulate or prevent a contraction of the particular muscle, and the controller is adapted to control the neural stimulator according to a neural stimulation protocol to control the contraction of the particular muscle.

* * * * *

UNITED STATES PATENT AND TRADEMARK OFFICE
CERTIFICATE OF CORRECTION

PATENT NO. : 7,616,990 B2 Page 1 of 1
APPLICATION NO. : 11/256907
DATED : November 10, 2009
INVENTOR(S) : Chavan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 758 days.

Signed and Sealed this

Nineteenth Day of October, 2010

David J. Kappos
*Director of the United States Patent and Trademark Office*